United States Patent
Ge et al.

(10) Patent No.: US 7,918,944 B2
(45) Date of Patent: Apr. 5, 2011

(54) SURFACE CARBURIZATION TECHNIQUE OF MEDICAL TITANIUM ALLOY FEMORAL HEAD IN HIP ARTHROPLASTY

(75) Inventors: Shirong Ge, Xuzhou (CN); Yong Luo, Xuzhou (CN)

(73) Assignee: China University of Mining and Technology (CN)

( * ) Notice: Subject to any disclaimer, the term of this patent is extended or adjusted under 35 U.S.C. 154(b) by 469 days.

(21) Appl. No.: 12/101,024

(22) Filed: Apr. 10, 2008

(65) Prior Publication Data

US 2008/0257455 A1    Oct. 23, 2008

(30) Foreign Application Priority Data

Apr. 10, 2007 (CN) .......................... 2007 1 0020889

(51) Int. Cl.
*C23C 8/00* (2006.01)
*C23C 14/00* (2006.01)
(52) U.S. Cl. .................. 148/223; 148/237; 148/421
(58) Field of Classification Search .................. 148/223, 148/237, 421; 420/420
See application file for complete search history.

(56) References Cited

FOREIGN PATENT DOCUMENTS

JP         2004010979 A   *   1/2004

OTHER PUBLICATIONS

Tanaka, English machine translation of JP 2004-010979A, 2004.*
Kim, et al., "Characterization of Ti-6A1-4V alloy modified by plasma carburizing process," Materials Science and Engineering A361 (2003) pp. 275-280.
Vadiraj, et al., "Effect of surface treatments on fretting fatigue damage of biomedical titanium alloys," Tribology International 40 (2007) pp. 82-88.
Österle, et al., "Potential of wear resistant coatings on Ti-6A1-4V for artificial hip joint bearing surfaces," Wear 264 (2008) pp. 505-517.
Niinomi, "Mechanical biocompatibilities of titanium alloys for biomedical applications," Journal of the Mechanical Behavior of Biomedical Materials 1 (2008) pp. 30-42.

* cited by examiner

*Primary Examiner* — Roy King
*Assistant Examiner* — Caitlin Fogarty
(74) *Attorney, Agent, or Firm* — Christie, Parker & Hale, LLP

(57) ABSTRACT

A surface carburization technique of medical titanium alloy femoral head in total hip arthroplasty comprises subjecting medical titanium alloy TC4 to surface carburization by using acetylene as carburizing agent to carry out gaseous carburization at high temperature to give medical titanium alloy femoral head in total hip arthroplasty with TiC ceramic on surface thereof. The TiC ceramic layer on femoral head can be more than 100 micron thick, which is relatively thick, overcomes the disadvantages in available medical titanium alloy material, and is particularly useful for replacement of total hip or knee arthroplasty.

1 Claim, No Drawings

SURFACE CARBURIZATION TECHNIQUE OF MEDICAL TITANIUM ALLOY FEMORAL HEAD IN HIP ARTHROPLASTY

CROSS-REFERENCE TO RELATED APPLICATION(S)

This application claims priority to and the benefit of Chinese Patent Application No. 200710020889.X filed in the Intellectual Property Office of the People's Republic of China on Apr. 10, 2007, the entire content of which is incorporated herein by reference.

FIELD OF THE INVENTION

The present invention relates to a surface carburization technique of medical titanium alloy femoral head in hip arthroplasty, particularly relates to the preparation of low-wearing titanium alloy femoral head in hip arthroplasty used in replacement of human body hip arthroplasty or knee arthroplasty.

BACKGROUND OF THE INVENTION

Since Branemark adopted titanium alloy as oral implant in sixties of the 20th century, titanium alloy has ended history as a material solely for aerospace application, and gained wide development and application in the field of biomedical material. Presently, Ti-6Al-4V alloy, also called TC4 titanium alloy, is the most widely used material in orthopedics. It is widely used as restoration material for surgery since it has excellent corrosion resistance, very good biocompatibility, high mechanical strength, and good machinability. However, research has shown Ti-6Al-4V alloy has low plastic shear resistance and undesirable work-hardening property, which is insufficient to resist friction wearing due to mechanical property impact. What's more, the $TiO_2$ film on surface is prone to peeling, and then can not well protect the subsurface layer. Usually under normal condition, the titanium alloy will form a stable and continuous oxide passivation film on surface which possesses good corrosion resistance. But due to the complexity of human body environment and erosion of external force and body fluid, the surface passivation film could be peeled and dissolved. Therefore some substances will be released into the tissue in use. Moreover, the titanium alloy has a large friction coefficient, which leads to poor wearing resistance. Therefore large amount of Ti, Al and V black debris will be generated due to wearing of the implant, and those debris can cause sterile loosening and lead to the failure of the joint replacement.

In order to improve the performance of the medical titanium alloy, various surface treatment methods were used to modify titanium alloy surface to make it more suitable for medical application. The surface modification of the titanium alloy not only keeps characteristics of the titanium alloy as a basal body material, but also dramatically improves overall performance of the titanium alloy; thus becoming hot spot in the research of medical titanium alloy. As the development of ion implantation, plasma spraying, chemical plating, ion plating, Physical vapor deposition (PVD), Chemical vapor deposition (CVD), microarc oxidation, and laser fusion coating techniques, TiN, TiC, diamond-like-carbon (DLC), and $TiO_2$ ceramic coat with good resistance to wearing and corrosion can be formed on the titanium alloy surface to improve bio surface wearing resistance and corrosion resistance; hydroxylapatize (HA) or bioactive glass (BG) bioactive coat also can be formed on surface of titanium alloy to prevent V and Al ions contained in the titanium alloy from releasing into physiological environment, so as to improve biocompatibility of the material. Thus it is important to research surface modification technique of titanium alloy, prepare cermet with resistances to wearing and corrosion, and study the properties of biofriction in physiological environment for developing high performance artificial joint, prolonging service life of titanium alloy artificial joint, disclosing its lubrication mechanism, and further improving stability and reliability of the artificial joint replacement.

SUMMARY OF THE INVENTION

One embodiment of the present invention is a surface carburization technique of medical titanium alloy femoral head in hip arthroplasty to overcome the problems existed in prior techniques and improve wearing resistance and service life of the medical titanium alloy femoral head of hip arthroplasty.

One aspect of one embodiment of the present invention is directed toward a surface carburization technique for forming a medical titanium alloy femoral head for use in hip arthroplasty, the process includes placing a medical titanium alloy (TC4) femoral head in an acetone solution for a period of time, placing the medical TC4 femoral head in a vacuum carburization furnace, evacuating the vacuum carburization furnace to a first pressure, heating and maintaining a constant temperature in the furnace, introducing $C_2H_2$ to the heated vacuum carburization furnace until a second pressure is reached, evacuating and discharging the gas resulted from $C_2H_2$ decomposition, repeating the $C_2H_2$ replenishment and its decomposition evacuation at a time interval for a plurality of times to form a first processed medical TC4 femoral head, stopping the heating, stopping the $C_2H_2$ decomposition evacuation when the temperature in the furnace reaches an ambient temperature to form a second processed medical TC4 femoral head, removing the second medical TC4 femoral head from the furnace, and polishing the second medical TC4 femoral head.

According to one embodiment of the present invention, the surface carburization technique of medical titanium alloy femoral head in hip arthroplasty comprises:

a. Firstly placing medical titanium alloy TC4 femoral head in hip arthroplasty in an acetone solution, and cleaning by ultrasonics for about 30 min;

b. Placing the medical titanium alloy TC4 femoral head in a vacuum carburization furnace, evacuating to about 100 Pa, heating to about 1300° C., and holding the temperature constant;

c. $C_2H_2$ was introduced to the vacuum carburization furnace with the TC4 femoral head when the pressure reaches about 2000 Pa in the furnace;

d. Evacuating and discharging the gas resulted from $C_2H_2$ decomposition;

e. Repeat the step c and d about every about 30 min for about 4 times, then stop heating, but continuously evacuating;

f. Stopping evacuation when furnace temperature is cooled to about 25° C., and taking off the resultant titanium alloy TC4 femoral head;

g. Then the surface of the aforesaid femoral head is polished to obtain a resultant medical titanium alloy TC4 femoral head for use in hip arthroplasty with a polished TiC ceramic on surface thereof.

The inventive surface carburization technique of medical titanium alloy femoral head in total hip arthroplasty performs surface carburization to medical titanium alloy TC4 by using acetylene as carburizing agent to carry out gaseous carburization at high temperature to give medical titanium alloy femoral head in hip arthroplasty with TiC ceramic on surface thereof. The TiC ceramic layer on femoral head in one embodiment is more than 100 microns which is relatively thick and overcomes the disadvantages in prior medical titanium alloy material, and is particularly useful for replacement of hip or knee arthroplasty. According to present invention, the femoral head with TiC layer has wide practicability in the technical field since it has the advantages of low wearing, good biocompatibility, good corrosion resistance, easy to preparation, and low cost.

DETAILED DESCRIPTION OF THE INVENTION

One embodiment of the present invention is a surface carburization technique for forming a medical titanium alloy femoral head for use in hip arthroplasty. The technique includes cleaning a medical TC4 femoral head, putting the femoral head in a heated, vacuumed oven, introducing a stream of $C_2H_2$ into the oven, evacuating gas built up generated from $C_2H_2$ decomposition, and reintroducing a fresh supply $C_2H_2$ into the oven and evacuating its gas decomposition for a plurality of times to form a TiC layer on the medical TC4 femoral head.

According to an embodiment of the present invention, the medical TC4 femoral head is first placed in an acetone solution for a period of time to be cleaned. In one exemplary embodiment, the TC4 femoral head is placed in the acetone solution for about 30 minutes (or 30 minutes).

The clean femoral head is then placed in a vacuum carburization furnace to start a surface modification process. Next, the vacuum carburization furnace is evacuated to a first pressure and heated to a first temperature, which is being maintained throughout the process. Then, $C_2H_2$ is introduced to the heated vacuum carburization furnace until a second pressure is reached. As $C_2H_2$ decomposes its decomposition is discharged and evacuated from the oven. Another stream of $C_2H_2$ is then introduced and the resulting gas from the decomposition is evacuated and discharged. This replenishment of $C_2H_2$ and gas decomposition evacuation is repeated at a time interval for a plurality of times to form a first processed medical TC4 femoral head. According to one embodiment, the replenishment of $C_2H_2$ and evacuation of its decomposition is done at a time interval of about 30 minutes (or 30 minutes) for four times. The heating is then ceased allowing the temperature inside the furnace to reach a room or ambient temperature (or 25° C.). At that point, a second processed medical TC4 femoral head is formed. The second processed medical TC4 femoral head is then removed from the oven and is polished to form a final medical TC4 femoral head.

In one exemplary embodiment, the first temperature inside the oven is heated to and maintained at about 1300° C. (or 1300° C.). In one exemplary embodiment, the first pressure inside the oven is about 100 Pa (or 100 Pa) and the second pressure is about 2000 Pa (or 2000 Pa).

In one exemplary embodiment, the temperature of the furnace is held constant for about two hours (or 2 hours) after four cycles of replenishing the oven with $C_2H_2$ and evacuating its gas decomposition to form a layer of TiC on a surface of the first medical TC4 femoral head.

However, according to one exemplary embodiment, a layer of TiC is sufficiently formed on the surface of the first medical TC4 femoral head after four cycles of replenishment the furnace with $C_2H_2$. In another exemplary embodiment, the layer of TiC has a thickness of 100 microns or more.

EXAMPLE

Another aspect of an embodiment of the present invention is directed toward a surface carburization technique for forming a medical titanium alloy femoral head, which includes selecting a medical titanium alloy TC4, mechanically process the titanium alloy into a femoral head for hip arthroplasty with any one of various diameters suitable for human body hip arthroplasty. Ultrasonic cleaning the femoral head in acetone for 30 min, placing it in a high temperature carburization furnace, evacuating the furnace to about 100 Pa, heating the furnace to 1300°, and holding the temperature constant; immediately introducing $C_2H_2$ into the furnace cavity until pressure reaches of about 2000 Pa, stopping the introduction of $C_2H_2$, evacuating, discharging the gas resulted from $C_2H_2$ decomposition; repeating the above process about every 30 min, holding the temperature for about 2 hours, in one embodiment after introducing $C_2H_2$ for four times, stopping heating, stopping evacuation when the furnace temperature is cooled to about 25° C., and taking out of the furnace the titanium alloy femoral head; polishing the surface of the femoral head, and sterilizing it for use in clinical application.

The femoral head has the advantages of low wearing, good biocompatibility, good corrosion resistance, simple preparation, low cost, and wide practicability in the technical field.

What is claimed is:

1. A surface carburization technique for forming a medical titanium alloy femoral head for use in hip arthroplasty, comprising:
   a. placing a medical titanium alloy TC4 femoral head in an acetone solution, and cleaning by ultrasonics for about 30 min;
   b. placing the medical titanium alloy TC4 femoral head in a vacuum carburization furnace, evacuating the furnace to about 100 Pa, heating the furnace to about 1300° C., and holding the temperature constant;
   c. introducing $C_2H_2$ in the vacuum carburization furnace forming a TiC ceramic on the femoral head until the pressure reaches to about 2000 Pa in the furnace;
   d. evacuating and discharging gas resulting from $C_2H_2$ decomposition;
   e. repeat the steps c and d about every 30 min for about 4 times, then stop heating, while continuously evacuating;
   f. stopping evacuation when furnace temperature is cooled to about 25° C., and taking out from the furnace the resulting medical titanium alloy TC4 femoral head; and
   g. then polishing the surface of the resulting femoral head to obtain the medical titanium alloy TC4 femoral head for use in hip arthroplasty with a TiC ceramic surface thereon.

* * * * *